United States Patent [19]

Johnson et al.

[11] 3,994,985

[45] Nov. 30, 1976

[54] CARBON BLACK CATALYSIS

[75] Inventors: Morris A. Johnson; Charles M. Starks; Kang Yang, all of Ponca City, Okla.

[73] Assignee: Continental Oil Company, Ponca City, Okla.

[22] Filed: Dec. 26, 1974

[21] Appl. No.: 536,710

Related U.S. Application Data

[63] Continuation of Ser. No. 278,884, Aug. 9, 1972, abandoned.

[52] U.S. Cl. .............................................. 260/658 R
[51] Int. Cl.² ......................................... C07C 17/20
[58] Field of Search ................................. 260/658 R

[56] References Cited
UNITED STATES PATENTS

| | | | |
|---|---|---|---|
| 2,675,413 | 4/1954 | Ballard et al. | 260/658 R |
| 3,130,222 | 4/1964 | Asadorian et al. | 260/658 R |
| 3,641,172 | 2/1972 | Johnson et al. | 260/658 R |
| 3,812,211 | 5/1974 | Johnson et al. | 260/658 R |

FOREIGN PATENTS OR APPLICATIONS 18,814   10/1966   Japan ............................. 260/658 R

OTHER PUBLICATIONS

Phase Transfer Catalysis, Starks, JACS 93, pp. 195–199 (1971).

Primary Examiner—Delbert E. Gantz
Assistant Examiner—Joseph A. Boska
Attorney, Agent, or Firm—Richard W. Collins

[57] ABSTRACT

Certain organic or organic-aqueous halide exchange reactions are catalyzed by carbon black.

4 Claims, No Drawings

CARBON BLACK CATALYSIS

This is a continuation of application Ser. No. 278,884, filed 8-9-72, now abandoned.

This invention relates to halide exchange reactions between halohydrocarbons, i.e. a hydrocarbon having a halide substituent, and between a halohydrocarbon and a halide compound soluble in an aqueous phase, e.g. an inorganic halide such as alkali metal halide, catalyzed by carbon black.

Organic and inorganic halide compounds are known and used for various purposes. Such halides are described in U.S. Pat. Nos. 1,891,415; 2,034,292; and 2,347,000. Such compounds are used as additives or solvents.

It is also known to produce desired halide compounds by a halide exchange reaction using a second compound to supply the desired halide. Typical exchange reactions are described in Phase Transfer Catalysis, Journal of the American Chemical Society, 93:1, pp. 195–199, January 1971.

Halide exchange reactions have been catalyzed by various agents such as quaternary ammonium and phosphonium salts, aluminum, activated coke and charcoal. These prior art reactions and catalysts require precise control of reaction conditions, reactant impurities and expensive catalyst preparation.

A halide exchange reaction process and catalyst have been discovered which do not require the precise control of the prior art processes and do not require an expensive catalyst.

According to this invention, there is provided a process for producing a compound having at least one X substituent where said X substituent is a halide comprising mixing in the presence of carbon black a first compound comprising a hydrocarbon having at least one Y substituent where Y is a halide other than X with a second compound capable of supplying an X anion and recovering said first compound having said X substituent. X and Y are preferably halides selected from iodine, bromine and chlorine.

The halide exchange reaction can produce simple exchange products or a complex mixture of halide compounds. The possible combinations are illustrated by the following equations:

$$R'X + R''Y \leftrightarrow R'Y + R''X \quad (I)$$

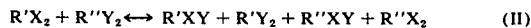

$$R'X_2 + R''Y_2 \leftrightarrow R'XY + R'Y_2 + R''XY + R''X_2 \quad (II)$$

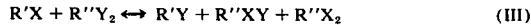

$$R'X + R''Y_2 \leftrightarrow R'Y + R''XY + R''X_2 \quad (III)$$

wherein R' is hydrocarbon radical, R'' is a hydrocarbon radical or an inorganic cation, and X and Y are halides. R' and R'' can be the same or different hydrocarbon radicals. X and Y are different halides.

In a preferred process both halide compounds are substituted hydrocarbons which mix in to a homogeneous phase. For some substituted hydrocarbons a solvent may be desired. Other process conditions are conventional and may be varied to affect the reaction in conventional manner.

In another preferred process the first halide compound is a substituted hydrocarbon and the second compound is an inorganic halide. Thus, the first compound forms an organic phase and the second can be added as a solid salt, dissolved in an aqueous phase or as a second liquid phase. Since the carbon black catalyst is a solid, a two-phase system will require vigorous mixing to be sure both phases and the carbon black are thoroughly mixing. The preferred halides for both compounds are iodine, bromine, and chlorine. Fluorine is not preferred because of the more severe reaction conditions required to substitute this halide.

The first halide compound of this invention comprises a hydrocarbon radical having a halide substituent that can be replaced. The hydrocarbon radical of the halohydrocarbon can be of any size and configuration that does not interfere with the reaction but low molecular weight hydrocarbons, such as $C_1$–$C_{14}$ hydrocarbons are preferred. These hydrocarbons can be alkyl, aryl, alicyclic and combinations thereof. Preferably the alkyls are $C_1$–$C_{10}$, the aryls are $C_6$–$C_{14}$, and the alicyclic radicals are $C_6$–$C_{14}$. The hydrocarbon group can also be alkenyl or contain some unsaturation as long as it does not interfere with the reaction. Groups which stabilize halide substitution, such as vinyl, do interfere with the reaction, therefore, reactive olefinic groups must be avoided or precautions taken to prevent interference. Likewise, the hydrocarbon radical can contain other substituents that do not interfere with the reaction.

The second halide compound can be any compound that can be mixed with the other components and is capable of supplying the desired X halide anion. The compound can be a hydrocarbon as described above having an X substituent. The compound can also be an inorganic salt such as a halide salt of a metal, including alkali metals and alkaline earth metals. In a preferred process using an immiscible aqueous phase a halide salt is a convenient and inexpensive source of the desired halide. A preferred process combines a halohydrocarbon as an organic phase with the second compound in an aqueous phase or aqueous media which forms an unstable emulsion or an emulsion which separates when mixing is stopped.

The carbon black catalyst used in the process of this invention has unexpected catalytic activity without requiring pretreatment or activation. Where lightly crystalline, porous and activated carbons such as graphite, charcoal and coke have been used as catalysts, it is unexpected that amorphous, relatively low surface, small particle carbon black can be used as a catalyst for a halide exchange reaction and especially in a hydrocarbon system. Any type of the numerous carbon blacks can be used but high surface area channel and furnace blacks are preferred. The low surface area thermal blacks can also be used. Surface area of carbon blacks vary from about 5–1000 square meter per gram carbon black by nitrogen adsorption. Preferred furnace blacks have a surface area in the range of about 20–300 sq.m/gm. Most commercially available rubber or ink grade carbon black can be used directly in the process of this invention. It may be desirable to remove hydrocarbon soluble extracts from certain thermal blacks and oil extended carbon black. The catalyst can be used in the process of this reaction in any amount to give the desired reaction rate as long as the carbon black does not interfere with the mixing and other aspects of the reaction. Up to about 5% by weight carbon black is preferred for reasonable reaction and mixing conditions. Due to the tendency of carbon black to adsorb halide and hydrocarbon high concentration should be avoided.

The other reaction conditions are conventional for a halide exchange reaction. The pressure is preferably autogenous. Temperatures in the range of about 0°–300° C can be used. An inert gas blanket is not required for most reactants but can be used if desired or required by a particular component.

In the following illustrative examples, parts percentage, and concentration is by weight unless indicated otherwise.

EXAMPLE 1

In a nickel autoclave 5 gram (gm) of ash-free gas furnace carbon black, 27.32 gm of 1,2-dibromoethane (145 millimole) and 11.85 gm ethylchloride (184 mm) are mixed and heated to about 150° C. The mixture is agitated at 125 rpm and maintained at 150° C for 30 minutes. The mixture is then distilled over a period of about one hour into a liquid nitrogen cooled glass bomb. The components are analyzed by gas chromatography using an n-octane standard and the following components are found:
- 6.71 gm ethylchloride
- 2.32 gm ethylbromide
- 0.37 gm 1,2-dichloroethane
- 3.71 gm 1-bromo-2-chloroethane, and
- 17.93 gm 1,2-dibromoethane This corresponds to an 82% recovery of bromide, a 75% recovery of chloride and a 34% conversion of 1,2-dibromoethane.

EXAMPLE 2

In a reactor as in Example 1, 5 gm of ash-free gas furnace carbon black, 24.74 gm of saturated aqueous sodium chloride solution (110 milliequivalents), and 10.05 gm 1,2-dibromoethane (53.5 mm) are mixed and heated to 150° C. After maintaining at 150° C for 30 minutes, the product mixture is separated from the aqueous phase using n-pentane and analyzed as in Example 1. The product contains:
- 1.18 gm 1,2-dichloroethane
- 2.09 gm 1,bromo-2-chloroethane, and
- 3.91 gm 1,2-dibromoethane This corresponds to an 88% recovery of the ethylene moiety and a 6% conversion of 1,2-dibromoethane.

I claim:
1. A process for producing a halohydrocarbon having at least one X substituent where X is selected from the group consisting of iodine, bromine and chlorine comprising mixing in the presence of a carbon black a halohydrocarbon having at least one Y substituent where Y is a halide other than X and selected from the group consisting of iodine, bromine and chlorine and wherein the hydrocarbon radical of said halohydrocarbon is selected from the group consisting of alkyl radicals having from one to ten carbons with an aqueous solution of an inorganic halide wherein the halide of said inorganic halide is X, and recovering a halohydrocarbon having at least one X substituent.

2. The process of claim 1 wherein said inorganic halide is an alkali metal halide.

3. The process of claim 1 wherein said alkali metal halide is sodium chloride and said halohydrocarbon having at least one Y substituent is 1,2-dibromoethane.

4. The process of claim 3 wherein said carbon black has a surface area in the range of about 20 to 300 $m^2/gm$.

* * * * *